(12) United States Patent
Porrata et al.

(10) Patent No.: US 6,953,440 B2
(45) Date of Patent: Oct. 11, 2005

(54) AUTOMATIC APPARATUS AND METHOD FOR TREATING CARPAL TUNNEL SYNDROME

(75) Inventors: Humberto Luis Porrata, Fort Lauderdale, FL (US); Alejandro Alberto Porrata, Miami, FL (US)

(73) Assignee: Porrata Group LLP, Pompano Beach, FL (US)

( * ) Notice: Subject to any disclaimer, the term of this patent is extended or adjusted under 35 U.S.C. 154(b) by 0 days.

(21) Appl. No.: 10/228,899

(22) Filed: Aug. 27, 2002

(65) Prior Publication Data

US 2003/0130692 A1 Jul. 10, 2003

Related U.S. Application Data

(60) Provisional application No. 60/315,154, filed on Aug. 27, 2001.

(51) Int. Cl.$^7$ .............................. A61H 23/04; A61F 5/01
(52) U.S. Cl. .......................... 601/149; 601/152; 602/13; 602/21
(58) Field of Search ................................ 601/148, 151, 601/152; 606/204, 202; 602/13, 21

(56) References Cited

U.S. PATENT DOCUMENTS

| | | | |
|---|---|---|---|
| 2,388,330 A | | 11/1945 | Jungmann |
| 2,823,668 A | | 2/1958 | Van Court et al. |
| 2,943,859 A | * | 7/1960 | Koski .......................... 473/214 |
| 4,067,063 A | | 1/1978 | Ettinger |
| 4,378,009 A | | 3/1983 | Rowley et al. |
| 4,479,648 A | | 10/1984 | Alivo |
| 4,787,376 A | | 11/1988 | Eisenberg |
| 4,899,763 A | * | 2/1990 | Sebastian et al. ........... 128/878 |
| 4,941,460 A | | 7/1990 | Working |
| 5,014,689 A | | 5/1991 | Meunchen et al. |
| 5,152,302 A | * | 10/1992 | Fareed ........................ 128/878 |
| 5,256,136 A | | 10/1993 | Sucher |
| 5,279,545 A | | 1/1994 | Reese, Sr. |
| 5,366,436 A | | 11/1994 | Gibney |
| 5,385,537 A | | 1/1995 | Davini |
| 5,405,357 A | | 4/1995 | Rowe-Lanzisera et al. |
| 5,413,553 A | | 5/1995 | Downes |
| 5,417,645 A | | 5/1995 | Lemmen |
| 5,441,058 A | | 8/1995 | Fareed |
| 5,468,220 A | | 11/1995 | Sucher |

(Continued)

FOREIGN PATENT DOCUMENTS

EP         0 861 651 A1    9/1998
WO      WO 97 23176 A    7/1997

*Primary Examiner*—Danton DeMille
(74) *Attorney, Agent, or Firm*—Bryan Cave LLP

(57) ABSTRACT

The apparatus of the present invention stretches the carpal ligament and the flexor retinaculum, as well as the superficial structures and muscles of the hand, in a safe manner under precise control of the patient or a healthcare professional. A first embodiment of the inventive apparatus includes a housing for receiving the patient's hand with pressure elements in contact with the hypothenar, thenar and central longitudinal dorsal portions of the patient's hand. Active pressure sources are provided for the pressure elements and connected to an automatic control unit. The control unit causes the inventive apparatus to delivered therapeutic treatment to the hand by selectively activating the active pressure sources causing the thenar and hypothenar regions of the hand to be pulled apart and upward around the dorsally positioned pressure element in accordance with program instructions indicative of a treatment plan. The inventive apparatus may include a variety of optional devices, such as a memory for storing program instructions and patient data, a display device for displaying operational parameters of the apparatus, and an output device for providing a record of the treatment.

20 Claims, 1 Drawing Sheet

U.S. PATENT DOCUMENTS

| | | | |
|---|---|---|---|
| 5,584,854 A | 12/1996 | Minarik | |
| 5,613,941 A | 3/1997 | Prengler | |
| 5,647,850 A | 7/1997 | Allen | |
| 5,672,150 A | 9/1997 | Cox | |
| 5,702,355 A | 12/1997 | Repice et al. | |
| 5,707,345 A | 1/1998 | Fulk | |
| 5,810,753 A * | 9/1998 | Eberbach | 602/21 |
| 5,897,549 A | 4/1999 | Tankovich | |
| 5,925,007 A | 7/1999 | Ashline | |
| 5,950,628 A | 9/1999 | Dunfee | |
| 6,029,277 A | 2/2000 | Picchione, II | |
| 6,120,472 A | 9/2000 | Singer, Jr. | |
| 6,146,347 A * | 11/2000 | Porrata | 602/21 |
| 6,179,800 B1 * | 1/2001 | Torrens | 602/21 |
| 6,200,286 B1 * | 3/2001 | Zamani | 602/64 |
| 6,213,969 B1 | 4/2001 | MacMorran et al. | |
| 6,217,536 B1 | 4/2001 | Gustafson | |
| 2002/0072786 A1 | 6/2002 | Gordon | |
| 2003/0018286 A1 * | 1/2003 | Porrata et al. | 602/21 |
| 2003/0028136 A1 * | 2/2003 | Stager | 602/21 |
| 2003/0125690 A1 | 7/2003 | Porrata | |
| 2003/0125691 A1 | 7/2003 | Porrata | |
| 2003/0130604 A1 | 7/2003 | Porrata | |
| 2003/0130652 A1 | 7/2003 | Porrata | |

\* cited by examiner

AUTOMATIC APPARATUS AND METHOD FOR TREATING CARPAL TUNNEL SYNDROME

This application claims the benefit of U.S. Provisional Application Ser. No. 60/315,154, filed Aug. 27, 2001. This application is related to four concurrently filed co-pending patent applications, namely U.S. Ser. No. 10/228,395 filed Aug. 27, 2002, entitled Non-Invasive Apparatus and Method for Treating Carpal Tunnel Syndrome, U.S. Ser. No. 10/228,739 filed Aug. 27, 2002, entitled Adjustable Apparatus and Method for Treating Carpal Tunnel Syndrome, U.S. Ser. No. 10/229,230 filed Aug. 27, 2002, entitled Adaptable Apparatus and Method for Treating Carpal Tunnel Syndrome, U.S. Ser. No. 10/228,738 filed Aug. 27, 2002, entitled Configurable Apparatus and Method for Treating Carpal Tunnel Syndrome, as well as co-pending U.S. patent application Ser. No. 10/199,747, entitled Apparatus and Method for Treating Carpal Tunnel Syndrome, filed Jul. 18, 2002, the contents of which are all hereby incorporated herein by reference.

FIELD OF THE INVENTION

This invention relates generally to treatment of carpal tunnel syndrome, and more particularly to a non-invasive apparatus and method for treatment of carpal tunnel syndrome.

BACKGROUND OF THE INVENTION

Carpal tunnel syndrome is a physiological disorder that afflicts over 850,000 people each year in the United States alone. In order to better understand the cause of the carpal tunnel syndrome and the difficulty in treating this serious disorder, a detailed explanation of the physiological factors and causes of carpal tunnel syndrome is presented below. Carpal tunnel syndrome is caused by a deleterious increase in pressure on the median nerve which passes through the carpal tunnel (or canal) in the hand, adjacent to the wrist. The deleterious increase in pressure, which is commonly brought on by prolonged repetitive motion of the hand and digits, is often caused by inflammation or damage to tendons for the hand which pass through the carpal tunnel along with the median nerve. Pressure increases can also be caused by narrowing of the carpal canal and by generalized swelling of the structures in the hand. Thus, when the carpal tunnel is narrowed from ligament shortening, muscle development or structural inflammation, the median nerve is undesirably compressed.

The carpal tunnel is formed by the eight carpal bones of the hand adjacent the wrist, which bones are arranged in two rows forming a generally U-shaped inverted arch-like "tunnel" structure. The three large carpal bones of the proximal row (i.e., closest to the chest), beginning laterally (i.e., from the outside with the hand directed downward and the palm facing forward), are the scaphoid, lunate, and triquetrum; the smaller pisiform bone sits on the palmar surface of the triquetrum. The distal row, from lateral to medial, consists of the trapezium, trapezoid, capitate, and hamate carpal bones. The vault of the carpal tunnel is formed by the carpal ligament and the flexor retinaculum. Nine tendons, their tendon sheaths, and the median nerve pass through the tunnel.

The carpal ligament is made of collagen and elastin and extends from the pisiformis and hamulus of hamate bones on the ulnar aspect of the tunnel to the tubercle (i.e., projection) of trapezium and the tubercle of the scaphoid bones on the radial (i.e. lateral) aspect of the carpal tunnel. The flexor retinaculum also stretches across the carpal tunnel and attaches to, on the medial aspect of the carpal tunnel, the pisiform bone and the hook of hamate, and, on the lateral aspect, the tubercle of the scaphoid and trapezium bones. The proximal border of the flexor retinaculum corresponds generally to the transverse skin crease at the base of the hand/wrist. The carpal ligament and flexor retinaculum, along with the carpal bones, form the restricted space through which the median nerve and several tendons pass.

Symptoms of carpal tunnel syndrome include tingling sensation in the hand, discomfort, numbness, and pain localized in the hand or radiating up the arm to the shoulder. All of these symptoms can occur during the day or can make the patients wake up at night. In advanced cases, there is atrophy and weakness of the thenar area of the hand which may weaken the grip and cause objects to fall out of the hand.

Conventional treatment of carpal tunnel syndrome is divided into surgical (invasive) and conservative (non-invasive). Surgical treatment consists of making an incision on the palmar aspect of the hand and splitting the carpal ligament, thus partially opening the carpal tunnel and relieving the pressure. This procedure, while occasionally successful, often has negative consequences, which include, but are not limited to, non-resolution of symptoms often requiring a second surgery, pain in the area of the scar, and injury to the superficial palmar branch of the median nerve causing persistent neurologic symptoms such as loss of full control over the hand. Furthermore, this procedure is very expensive. Understandably, surgical treatment is often considered as a last option.

Conservative, non-invasive treatment is typically separated into three categories—mild, moderate and alternative. Mild treatments may involve the use of anti-inflammatory medications, application of resting hand splints, physical therapy, modification of patient's activities that cause the condition, and even a change in the patient's job. Moderate treatments involve one or more mild treatments coupled with cortisteriod injections. Finally, alternative methods include acupuncture, massage, application of magnets, tai-chi exercises, and the like.

However, none of the above treatments have produced uniformly positive results. While some treatments may alleviate the symptoms of carpal tunnel syndrome in individual patients, the symptoms often return when the course of treatment is terminated. Furthermore, one of the main disadvantages of the various treatment approaches is that they must be delivered by a healthcare provider such as a physician or a physical or occupational therapist. This adds a significant level of inconvenience to the patient who must allocate time to visit the healthcare provider for injections and/or physical therapy. Medications that are used to provide relieve from the pain and discomfort caused by carpal tunnel syndrome also suffer from a number of disadvantages. For example, certain medications have undesirable side effects or interactions with the patient's other medications, if any.

As a result, a number of techniques for treating carpal tunnel syndrome that address at least some of the above problems have been developed over the years. Some merely maintain the patient's hand in a neutral position (such as the device disclosed in U.S. Pat. No. 5,014,689) to prevent the symptoms from worsening. Another approach involved mechanical stretching of the carpal ligament, as disclosed in U.S. Pat. No. 5,256,136. Yet another series of techniques advocated placement of a compression bracelet on the forearm (U.S. Pat. No. 5,441,058), or on the wrist (U.S. Pat. No. 5,468,220) to apply a predetermined pressure on certain portions of the forearm, or wrist, respectively, in order to widen the carpal tunnel and thus provide relief to the patient suffering from carpal tunnel syndrome.

However, the above-described previously known devices suffer from a crucial disadvantage. Application of pressure to different portions of the forearm and/or the wrist only has a minimal effect on widening the carpal tunnel, and may only provide temporary relief from carpal tunnel syndrome rather than eliminating or suppressing the condition.

Further development in the area of mechanical treatment of carpal tunnel syndrome continued, and eventually resulted in discovery of the Porrata principle, disclosed in the commonly assigned U.S. Pat. No. 6,146,347 to Humberto Porrata, that provides a novel and advantageous device and method for treating carpal tunnel syndrome that solve the problems posed by previously known devices and techniques. Most importantly, research conducted in conjunction with development of the Porrata device, has shown that carpal tunnel syndrome may be treated with great effectiveness by precise controlled transverse stretching of the carpal ligament and the flexor retinaculum. The U.S. Pat. No. 6,146,347 patent disclosed a splint-like device that fit over the patient's hand and a portion of the wrist. The device included rigid sections for contacting the thenar and hypothenar portions of the hand and a selectable active pressure source that, when actuated, applied pressure to the dorsal portion of the patient's hand opposed by the forces delivered by the thenar and hypothenar sections of the device in such a manner, as to transversely stretch the carpal ligament and the flexor retinaculum in a comfortable and controlled manner.

Nevertheless, the device of the U.S. Pat. No. 6,146,347 patent is susceptible to improvement. First because of its construction it generally must be fabricated in different sizes to fit various patients, and patients with unusual hand sized or shapes may need custom-fabricated devices. Second, it generally requires the patient or healthcare provider to monitor the use of the device to ensure that appropriate level of pressure was delivered during treatment for an appropriate level of time. Also, the healthcare provider must manually keep track of the treatment process.

It would thus be desirable to provide an apparatus and method for treating carpal tunnel syndrome by transversely stretching the carpal ligament and the flexor retinaculum of a patient's hand in a comfortable and controlled manner. It would further be desirable to provide an apparatus and method for treating carpal tunnel syndrome embodied in a device that is dynamically adaptable to patients of various physical characteristics. It would also be desirable to provide an automatic apparatus and method for treating carpal tunnel syndrome responsive to a course of treatment predetermined by a healthcare provider. It would additionally be desirable to provide an automatic apparatus and method for maintaining and/or producing records of previous treatment of carpal tunnel syndrome by the apparatus.

SUMMARY OF THE INVENTION

The apparatus and method of the present invention advantageously overcome the problems and drawbacks of previously known approaches for treating carpal tunnel syndrome. Similarly to the device disclosed in the commonly assigned U.S. Pat. No. 6,146,347 which is hereby incorporated by reference in its entirety, the main objective of the present invention is to apply the Porrata principle to stretch the carpal ligament and the flexor retinaculum, as well as the superficial structures and muscles of the hand, in a safe manner under precise control of the patient or a healthcare professional. However, the apparatus and method of the present invention enable the Porrata principle to be implemented in a device that may be readily used by patients with any size or shape hands. Furthermore, the inventive apparatus is very simple and inexpensive to manufacture.

The inventive apparatus dynamically treats carpal tunnel syndrome through automatically controllable selective application of pressure to large portions of the palm of the hand (in the thenar and hypothenar areas) while at the same time retaining the central dorsum of the hand, in essence providing pressure in the opposite direction. Alternately, active pressure is selectively applied to the central dorsum of the hand as well. This procedure stretches the carpal ligament, the flexor retinaculum, and superficial structures and muscles of the hand in the palmar aspect of the hand, in a readily, safely controllable and comfortable manner. The inventive apparatus delivers treatment in accordance with control instructions received from the user (for example, a healthcare provider).

Considering that the constitutions of the carpal ligament and the flexor retinaculum are soft tissue composed of collagen and elastin, stretching the carpal ligament and the flexor retinaculum is effective for decreasing compression on the median nerve by increasing the diameter of the tunnel and decreasing the rigidity of the retinaculum and the carpal ligament, thus alleviating the symptoms of carpal tunnel syndrome.

The preferred embodiment of the inventive apparatus commonly includes a housing for receiving the patient's hand with a bottom portion having a first pressure element adapted and configured to contact the hypothenar region of the patient's hand and a second pressure element adapted and configured to contact the thenar region of the patient's hand, and a top portion having a central longitudinal third pressure element adapted and configured to contact the central longitudinal dorsal region of the patient's hand. The first and second pressure elements are connected to active pressure sources (or source) controlled by a control unit. In response to predetermined instructions received from the operator (for example, a healthcare provider), the control unit activates the first and second pressure elements, when the hand is inserted into the housing, to exert pressure on the respective hypothenar and thenar regions of the hand while the central dorsal portion of the hand presses against the third pressure element. This forces the thenar and hypothenar regions apart, thus advantageously stretching the carpal ligament, the flexor retinaculum, and superficial structures and muscles of the hand. The predetermined instructions may include settings for the pressure levels for the first and second pressure elements, as well as a setting for the duration for which the pressure elements are to be activated. The apparatus may also include optional memory for storing the predetermined instructions for the control unit, as well as one or more output devices, such as a speaker, display screen and/or a printer for outputting data indicative of the operation of the apparatus.

In another embodiment of the present invention, the third pressure element is also connected to an active pressure source controlled by the control unit, such that active pressure is applied to the central dorsal region of the hand while the first and second pressure elements apply pressure to the hypothenar and thenar regions of the hand.

Because the various pressure elements are adjustable and configurable, the inventive apparatus is readily usable by patients with different hand shapes and/or sizes. Furthermore, the control unit of the inventive apparatus enables a healthcare provider to design and implement a course of treatment for each patient based on that patient's unique requirements to prevent progression of carpal tunnel syndrome and to provide relief from symptoms by increasing the cross sectional area of the carpal tunnel, thus decreasing compression on the median nerve and decreasing the resulting symptoms.

Other objects and features of the present invention will become apparent from the following detailed description considered in conjunction with the accompanying drawing. It is to be understood, however, that the drawing is designed solely for purposes of illustration and not as a definition of the limits of the invention, for which reference should be made to the appended claims.

BRIEF DESCRIPTION OF THE DRAWING

In the drawing, wherein like reference characters denote like elements throughout.

DETAILED DESCRIPTION OF PREFERRED EMBODIMENTS

Figure 1:
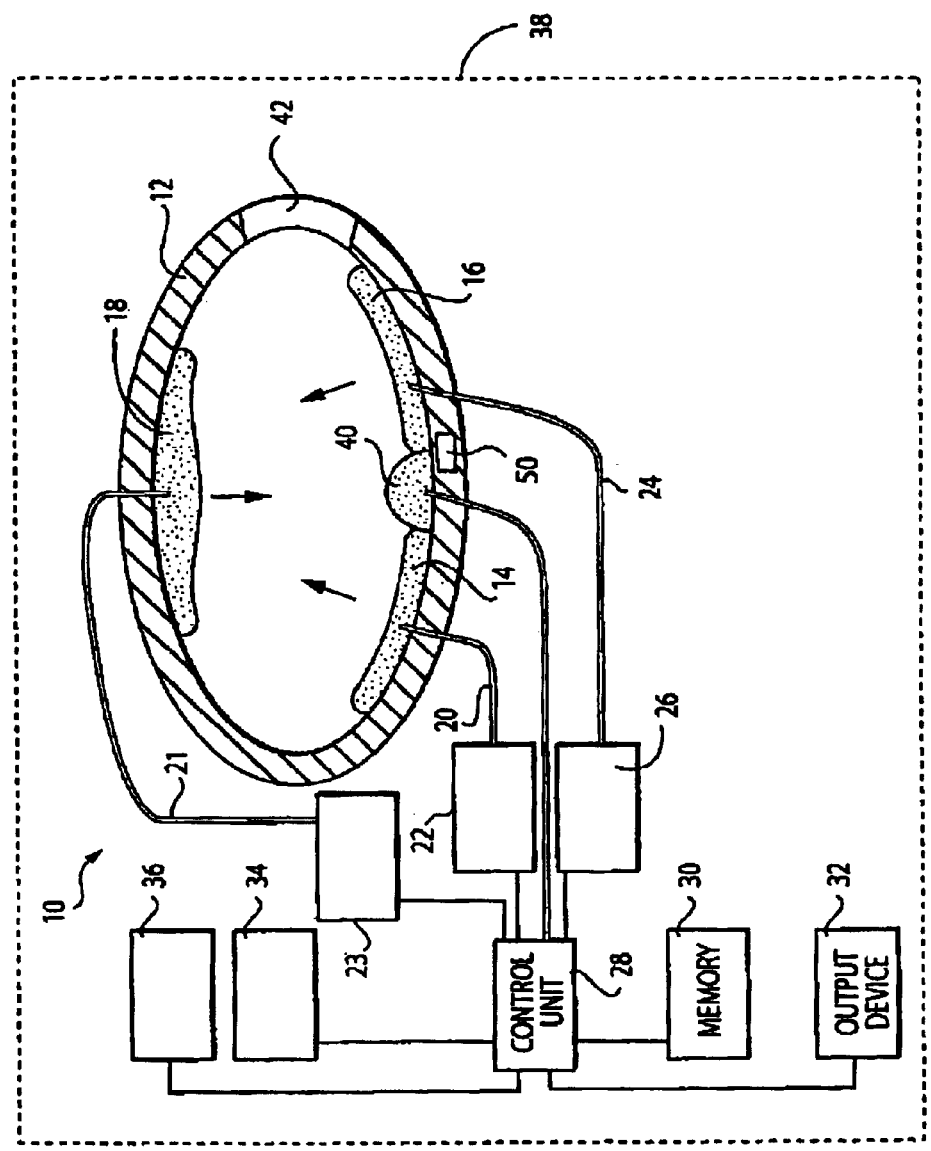
FIG. 1 is a schematic diagram of a preferred embodiment of the inventive automatic apparatus for treating carpal tunnel syndrome.

The present invention is described with reference to various materials that compose the inventive structures and elements thereof, and to various devices for selectively applying pressure to a specific area of the hand, by way of example only—it should be understood that the apparatus and method of the present invention may be utilized with any materials or selective pressure sources having properties similar to those described in the exemplary embodiments, without departing from the spirit of the invention.

The essence of the Porrata approach, disclosed and described in greater detail in the above-incorporated U.S. Pat. No. 6,146,347, involves applying pressure to a portion of the top surface of the hand (i.e., the central dorsal region), while at the same time applying opposing pressure to the thenar and hypothenar regions of the palm. The apparatus and method of the present invention advantageously implement the Porrata principle in a simple to use device that works equally well with different hand shapes and sizes.

Referring now to FIG. 1, a preferred embodiment of an inventive apparatus 10 is shown. The apparatus 10 includes a housing 12 having an internal hollow region, an internal central top portion having a first central longitudinal section, an internal bottom portion having a second longitudinal section and a parallel third longitudinal section and an open end portion for receiving the hand into the internal region such that the hypothenar region of the hand is substantially aligned with said second section, and the thenar region of the hand is substantially aligned with said third section. The housing 12 also includes a first active pressure element 14 for contacting the hypothenar region of the hand, a second active pressure element 16 for contacting the thenar region of the hand, and a pressure member 18 for contacting the longitudinal central dorsal portion of the hand. The housing 12 may be composed of a rigid material such as metal, hard plastic or wood, or a resilient material such as fiberglass or resilient plastic, or a combination thereof. The housing 12 may also include an optional hole 42 in a side wall thereof for receiving the patient's thumb. The housing 12 may further include an optional heat source 40, disposed between the first and the second active pressure elements 14, 16, for applying heat to the patient's palmar region during therapeutic use of the apparatus 10. The pressure member 18 may be composed of any rigid or resilient material, or a combination thereof.

The first active pressure element 14 is connected to a first pressure source 22 via a connector 20, while the second active pressure element 16 is connected to a second pressure source 26 via a connector 24. Alternately, the first and second pressure sources 22, 26 may be positioned proximal to the outer surface of the housing 12 and directly connected to the respective active pressure elements 14, 16 without the use of respective connectors 20, 24.

The first and second active pressure elements 14,16 may be any variable remotely controllable (singular or plural) pressure elements, such as air or fluid inflatable bladders, electromechanical pressure plates, or a combination thereof. The first and second pressure sources 22, 26 (and the connectors 20, 24) are selected to correspond to the respective first and second active pressure elements 14, 16 to provide the necessary source of pressure. For example, if the first and second active pressure elements 14, 16 are air-inflatable bladders, the first and second pressure sources 22, 26 are air pumps (and the connectors 20, 24 are air hoses). In another example, if the first and second active pressure elements 14, 16 are mechanically actuated plates, the first and second pressure sources 22, 28 are screw, puller or wedge mechanisms disposed on the housing 12. In this example, control over the delivered pressure is actuated by rotating the screw or puller mechanism(s), or by moving the wedge(s). In yet another example, if the first and second active pressure elements 14, 16 are electromechanically actuated plates (for example using electromagnets), the first and second pressure sources 22, 26 are electrical power sources (and the connectors 20, 24 are wires). Other types of active pressure elements, and corresponding pressure sources, may be utilized as a matter of design choice without departing from the spirit of the present invention. Alternately, both first and second pressure sources, 22, 26 may be embodied in a single unit for actuating both active pressure elements 14, 16. Optionally, the pressure member 18 may be replaced by an active pressure element, similar to the active pressure elements 14, 16, and connected via connector 21 to a third pressure source 23. In this manner, all pressure elements of the apparatus 10 may be made active.

A control unit 28, for controlling the operation of the apparatus 10, is connected to the first and second pressure sources 22, 26 (and optionally to the third pressure source 23 and the heat source 40). The control unit 28 may be a microprocessor, or a solid state device capable of executing program instructions and transmitting control signals to various components of the apparatus 10. Program instructions indicative of a treatment protocol selected by the healthcare provider may be delivered to the control unit 28 via an input device 34 connected thereto. The program instructions may include, but are not limited to: the magnitudes of pressure delivered by the pressure elements 14, 16, and, optionally 18, the duration of the delivered pressure, a number of cycles of repeated delivery of pressure, and whether or not heat is delivered to the region being treated, before, during, or after treatment (or in any combination of the three).

The input device 34 may be a set of keys (such as a keypad or a keyboard), selectable switches, dials, or a voice input system for interpreting voice instructions. The program instructions may then be stored in a memory 30. The memory 30 may be any device for retaining electronic data, such as a memory chipset, or the like. Alternately, instead of being entered or individually selected by the healthcare provider, the program instructions may be pre-stored in the memory 30, for example, in form of one or more treatment plans selectable by the healthcare provider via the input device 34. Optionally, the input device 34 may be utilized to enter information about the patient being treated to be stored in the memory 30. The control unit 28 may then optionally record the various settings (pressure levels, duration, etc.) of the apparatus 10, as well as the date of treatment, along with the patient information to maintain a record of the course of treatment by the apparatus 10.

An optional display device 36, such as a screen or another indicator, may also be connected to the control unit 28 for displaying the status of the apparatus 10 and of one or more operational parameters, such as time remaining for treatment, and/or pressure levels. The display device 36 may also display prompts for the healthcare provider to facilitate selection and/or entry of the program instructions. An optional output device 32, such as a printer, may be connected to the control unit 28 to output information about the settings of the apparatus 10 as well as any treatment records stored in the memory 30.

The apparatus 10 may also include an electronic device 50 that includes a laser or similar device adapted to specifically denature the proteins that make up the ligaments in the body, thus making it easier to stretch the ligaments. The electronic device 50 is preferably aligned with the flexor retinaculum or carpal ligament as the hand is placed in the apparatus 10. The electronic device 50 may also include conventional sensors to measure the amount of stretching of the flexor retinaculum or carpal ligament through, e.g., tension measurements or displacement of carpal bones. The laser and sensors may operate under control of the control unit 28.

Alternately, some or all components of the apparatus 10 may be disposed within a common housing 38.

To utilize the apparatus 10, a patient inserts their hand into the housing 12, such that the first active pressure element 14 contacts the hypothenar region of the palm and the second active pressure element 16 contacts the thenar region of the palm, while the pressure member 18 contacts the longitudinal central dorsal region of the hand. Optionally, the control unit 28 may prompt the patient to insert their hand, for example by way of displaying a prompt on the display device 36, or via a synthesized voice prompt delivered by a voice output device (not shown).

Once the patient inserts their hand, and an instruction is given to the control unit 28 to being treatment, the control unit 28 activates the pressure sources 22, 26, causing the active pressure elements 14, 16 to deliver upward pressure on the respective hypothenar and thenar regions of the hand while the pressure member 18 retains and presses downward against the central dorsal region. The first and said second upward forces are thus opposed by the downward force exerted by the pressure member 18 on the central dorsal region of the hand, such that the downward force is balanced and opposed by the first and second upward forces causing carpal bones of the hand to separate to transversely stretch the carpal ligament and the flexor retinaculum of the hand, thus implementing the Porrata principle to widen the carpal canal and provide treatment of carpal tunnel syndrome to the patient. The magnitude and duration of the pressure delivery are selected by the control unit 28 in accordance with the program instructions. Optionally, the control unit 28 may record the delivery of the treatment and its parameters in a patient record stored in the memory 30. An optional sensor (not shown) may be provided and connected to the control unit 28 for sensing when the hand is properly positioned within the housing 12, such that treatment is initiated by the control unit 28 automatically.

Thus, while there have been shown and described and pointed out fundamental novel features of the invention as applied to preferred embodiments thereof, it will be understood that various omissions and substitutions and changes in the form and details of the devices and methods illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. It is the intention, therefore, to be limited only as indicated by the scope of the claims appended hereto.

We claim:

1. An apparatus for treating carpal tunnel syndrome in a person's hand, the hand having a longitudinal axis, a palmar aspect with thenar and hypothenar regions, and a dorsal region opposed to the palmar aspect, the apparatus comprising:

a housing having an internal hollow region, an internal central top portion having a first ventral longitudinal section, an internal bottom portion having a second longitudinal section and a parallel third longitudinal section, and an open end portion for receiving the hand into said internal region such that the hypothenar region of the hand is substantially aligned with said second section, and the thenar region of the hand is substantially aligned with said third section;

contact means, disposed longitudinally along said first central longitudinal section, for contacting a central longitudinal portion of the dorsal region of the hand;

first pressure means, disposed along said second section so as to contact the hypothenar region of the hand when the hand is inserted into said housing, for selectively applying pressure of a first predetermined magnitude to the hypothenar region of the hand;

second pressure means, disposed along said third section so as to contact the thenar region of the hand when the hand is inserted into said housing, for selectively applying pressure of a second predetermined magnitude to the thenar region of the hand; and a control unit, connected to said first and said second pressure means, operable to:
  activate said first pressure means to apply a first upward force to the hypothenar region of the hand, and
  activate said second pressure means to apply a second upward force to the thenar region of the hand, wherein said first and said second upward forces are opposed by a downward force exerted by said contact means on the central dorsal region of the hand, such that said downward force is balanced and opposed by said first and said second upward forces causing carpal bones of the hand to separate to stretch a carpal ligament and a flexor retinaculum of the hand,
  wherein said control unit selectively activates said first and said second pressure means in response to predetermined program instructions.

2. The apparatus of claim 1, wherein said contact means comprises:

third pressure means, disposed along said first central longitudinal section so as to contact the central longitudinal dorsal region of the hand when the hand is inserted into said housing and connected to said control unit, for selectively applying pressure of a third predetermined magnitude to the central dorsal region of the hand, in response to a signal from said control unit, to provide a controllable source of said downward force.

3. The apparatus of claim 1, further comprising a memory, connected to said control unit, operable to store said predetermined program instructions.

4. The apparatus of claim 1, further comprising a display device, connected to said control unit, operable to display at least one parameter indicative of said predetermined program instructions.

5. The apparatus of claim 1, further comprising an input device, connected to said control unit, operable to receive said predetermined program instructions.

6. The apparatus of claim 1, wherein said predetermined program instructions further comprise values for said first and said second predetermined magnitude of pressure and a time interval value for which said control unit causes said first and said second pressure means to remain active.

7. The apparatus of claim 1, further comprising heating means, positioned between said first and said second pressure means and connected to said control unit, for delivering therapeutic heat to the palmer aspect of the hand during treatment in response to a signal from said control unit.

8. The apparatus of claim 1, wherein said housing, said first and said second pressure means and said control unit are disposed in a common housing.

9. The apparatus of claim 1 further comprising an electronic device comprising a laser adapted to denature proteins forming the flexor retinaculum and the carpal ligament.

10. The apparatus of claim 9 wherein the electronic device further comprises a sensor to measure the amount that the flexor retinaculum stretches.

11. An apparatus for treating carpal tunnel syndrome in a person's hand, the hand having a longitudinal axis, a palmar aspect with thenar and hypothenar regions, and a dorsal region opposed to the palmar aspect, the apparatus comprising:

a housing having an internal hollow region, an internal central top portion having a first central longitudinal section, an internal bottom portion having a second longitudinal section and a parallel third longitudinal section, and an open end portion for receiving the hand into said internal region such that the hypothenar region of the hand is substantially aligned with said second section, and the thenar region of the hand is substantially aligned with said third section;

a pressure member disposed longitudinally along said first central longitudinal section for contacting a central longitudinal portion of the dorsal region of the hand;

a first pressure element disposed along said second section so as to contact the hypothenar region of the hand when the hand is inserted into said housing, the first pressure element connected to a first active pressure source for selectively applying pressure of a first predetermined magnitude to the hypothenar region of the hand; and a second pressure element disposed along said third section so as to contact the thenar region of the hand when the hand is inserted into said housing, the second pressure element connected to a second active pressure source for selectively applying pressure of a second predetermined magnitude to the thenar region of the hand; and a control unit, connected to said first and said second pressure sources, operable to:
  activate said first pressure source to apply a first upward force to the hypothenar region of the hand, and
  activate said second pressure source to apply a second upward force to the thenar region of the hand, wherein said first and said second upward forces are opposed by a downward force exerted by said pressure member on the central dorsal region of the hand, such that said downward force is balanced and opposed by said first and said second upward forces causing carpal bones of the hand to separate to stretch a carpal ligament and a flexor retinaculum of the hand, wherein said control unit selectively activates said first and said second pressure source in response to predetermined program instructions.

12. The apparatus of claim 11, wherein said pressure member comprises:

a third pressure element disposed along said first central longitudinal section so as to contact the central longitudinal dorsal region of the hand when the hand is inserted into said housing, the third pressure element connected to a third pressure source for selectively applying pressure of a third predetermined magnitude to the hypothenar region of the hand to provide a controllable source of said downward force.

13. The apparatus of claim 11, further comprising a memory, connected to said control unit, operable to store said predetermined program instructions.

14. The apparatus of claim 11, further comprising a display device, connected to said control unit, operable to display at least one parameter indicative of said predetermined program instructions.

15. The apparatus of claim 11, further comprising an input device, connected to said control unit, operable to receive said predetermined program instructions.

16. The apparatus of claim 11, wherein said predetermined program instructions further comprise values for said first and said second predetermined magnitude of pressure and a time interval value for which said control unit causes said first and said second pressure sources to remain active.

17. The apparatus of claim 11, further comprising a heater positioned between said first and said second pressure elements and connected to said control unit, for delivering therapeutic heat to the palmar aspect of the hand during treatment in response to a signal from said control unit.

18. The apparatus of claim 11, wherein said housing, said first and said second pressure sources and said control unit are disposed in a common housing.

19. The apparatus of claim 11, further comprising an electronic device comprising a laser adapted to denature proteins forming the flexor retinaculum and the carpal ligament.

20. The apparatus of claim 19 wherein the electronic device further comprises a sensor to measure the amount that the flexor retinaculum stretches.

* * * * *